Figure 1:
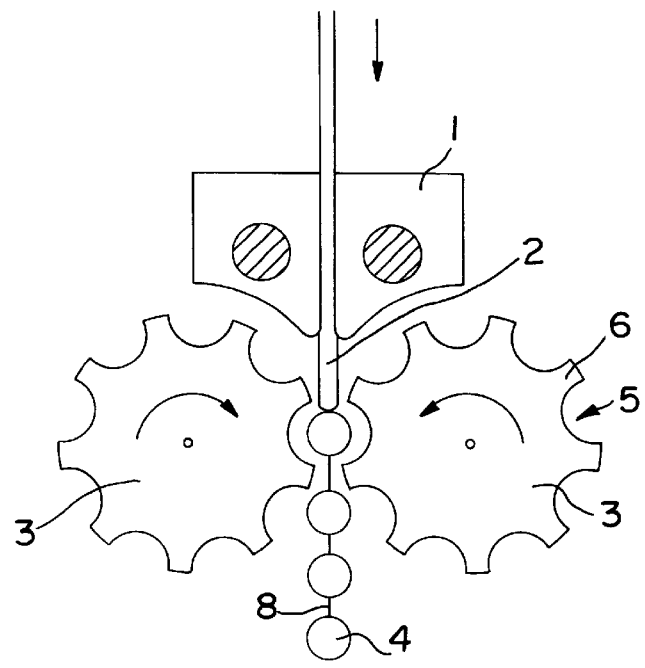

United States Patent
Breitenbach et al.

[11] Patent Number: 6,120,802
[45] Date of Patent: Sep. 19, 2000

[54] METHOD OF PRODUCING MULTI-LAYER MEDICAMENTS IN SOLID FORM FOR ORAL OR RECTAL ADMINISTRATION

[75] Inventors: Jörg Breitenbach, Mannheim; Axel Paul Härtl, Dirmstein; Jürgen Hofmann, Ludwigshafen; Joerg Rosenberg, Ellerstadt; Michael Schiessl, Hassloch; Hans Dieter Zettler, Grünstadt, all of Germany

[73] Assignee: BASF Aktiengesellschaft, Ludwigshafen, Germany

[21] Appl. No.: 09/051,544

[22] PCT Filed: Oct. 23, 1996

[86] PCT No.: PCT/EP96/04601

§ 371 Date: Apr. 15, 1998

§ 102(e) Date: Apr. 15, 1998

[87] PCT Pub. No.: WO97/15293

PCT Pub. Date: May 1, 1997

[30] Foreign Application Priority Data

Oct. 23, 1995 [DE] Germany ............... 195 39 361

[51] Int. Cl.$^7$ ............... A61K 9/20; A61K 9/28; A61K 9/36
[52] U.S. Cl. ............... 424/464; 424/474; 424/480
[58] Field of Search ............... 424/464, 465, 424/474; 514/966

[56] References Cited

U.S. PATENT DOCUMENTS

| | | |
|---|---|---|
| 4,801,460 | 1/1989 | Goertz et al. . |
| 4,880,585 | 11/1989 | Klimesch et al. . |
| 5,283,187 | 2/1994 | Aebischer et al. . |
| 5,681,583 | 10/1997 | Conte et al. ............... 424/472 |

FOREIGN PATENT DOCUMENTS

| | | |
|---|---|---|
| 0061217 | 9/1982 | European Pat. Off. . |
| 303 306 | 2/1989 | European Pat. Off. . |
| 89/12442 | 12/1989 | WIPO . |
| 91/10425 | 7/1991 | WIPO . |

*Primary Examiner*—Thurman K. Page
*Assistant Examiner*—S. Howard
*Attorney, Agent, or Firm*—Keil & Weinkauf

[57] ABSTRACT

The present invention relates to a process for producing multilayer, solid drug forms for oral or rectal administration, which comprises coextrusion of at least two compositions which in each case comprise a thermoplastic, pharmacologically acceptable polymeric binder which is soluble or swellable in a physiological environment, and at least one of which contains a pharmaceutical active ingredient, and shaping the coextruded multilayer material to the required drug form.

10 Claims, 1 Drawing Sheet

METHOD OF PRODUCING MULTI-LAYER MEDICAMENTS IN SOLID FORM FOR ORAL OR RECTAL ADMINISTRATION

The present invention relates to a process for producing multilayer, solid drug forms for oral or rectal administration, and to the drug forms obtainable by the process according to the invention.

Drug forms consisting of several layers, for example laminated or multilayer tablets, which may be coated, are increasingly being used, for example in order to combine active ingredients which are incompatible with one another or to bring about release of initial and maintenance doses in the case of controlled-release drug forms. Drug forms of these types are produced by classical methods. Thus, laminated tablets are produced by dry coating, and multilayer tablets are produced by compressing two or more layers of granules. Special machines are required therefor and resemble in their mode of operation the conventional rotary machines, with at least two filling and compressing stations being required. These conventional processes are therefore elaborate and cost-intensive.

A process for producing tablets which is considerably simpler than the classical multistage, batchwise tabletting process has been known for some time. It comprises taking up the active ingredient in a polymeric binder, extruding the polymer melt containing the active ingredient, and shaping the extrudate emerging from the extruder in a suitable manner, see, for example, EP-A-240 904 and 240 906.

Coextrusion is known in plastics technology and entails the melt streams from a plurality of extruders being combined in a mold so that the required layer structure of various thermoplastics results. The use of coextrusion in the drugs industry is mainly confined to the production of packaging films. In addition, the production of polymer capsules and coated active ingredients in the form of a fish medicine and of an implant is known:

WO-A-89/12442 describes a pharmaceutical dosage form for the medication of fish. As a rule, drugs are administered to fish via the feed, ie. the drug is mixed with the feed. The problem with this was that the drug-containing feed was not accepted by the fish because of its taste. The consequence of this was that a large part of the drug-containing feed remained in the water for a lengthy period, remained unused and could sink. This led to unwanted release of the drug into the water, which naturally led to contamination of the water.

To solve this problem, WO 89/12442 proposes a dosage form which is obtained by coextrusion and which consists of an outer layer which surrounds an inner chamber. The outer layer consists of a starch derivative which contains a suitable animal or vegetable material in order to make the dosage form acceptable to the fish. In addition, the outer layer is impermeable to water and to the active ingredient contained in the inner chamber. The inner chamber contains the active ingredient in a viscous suspension which only partly fills the chamber. This provides an air space which confers on the dosage form the necessary buoyancy for it not to sink but float in the water.

U.S. Pat. No. 5,283,187 describes an implant which comprises as active ingredient a cell suspension which is enclosed in a semipermeable polymer membrane. The implant is produced by coextrusion of the cell suspension with a solution of the polymer in a suitable water-miscible organic solvent. The polymer must be chosen so that it coagulates on extrusion and forms a network of channels so that the membrane becomes semipermeable.

EP-A-303 306 describes a cylindrical implant which has a core of an ethylene/vinyl acetate copolymer with a melt flow index of more than 10 g/10 min and a vinyl acetate content of at least 20% by weight. The core is surrounded by a membrane with a thickness of 50 bis 250 $\mu$m which likewise consists of an ethylene/vinyl acetate copolymer. This polymer has, however, a melt flow index of less than 10 g/10 min and a vinyl acetate content of less than 20% by weight. The membrane serves to control the release of the active ingredient contained in the core, a contraceptive, in such a way that the latter is released in a daily dose of 15 to 30 $\mu$g over a period of at least 2 years. The implant is produced by coextrusion of the two polymer layers.

The abovementioned implants are administered parenterally, for example subcutaneously. The outer layer of the implants is designed so that it does not dissolve in the body fluids, and the implant can therefore be removed again from the body in a simple manner.

The requirements to be met by a drug form which can be administered orally or rectally and which is intended to permit specific adjustment of the required active ingredient release characteristics are quite different from this. A drug form of this type is intended to release the active ingredient relatively rapidly, compared with an implant, in the required manner and at the required site and expediently to dissolve in body fluids.

It is an object of the present invention to provide solid drug forms which can be administered orally or rectally, and a process for producing them, which permits the drug form to be produced in a simple and mild manner, and the required release characteristics to be ensured.

We have found that this object is achieved by a multi-layer solid drug form which is obtainable by coextrusion of two compositions of a pharmaceutically acceptable thermoplastic polymer, at least one of which contains a pharmaceutical active ingredient.

The present invention therefore relates to a process for producing multilayer, solid drug forms for oral or rectal administration, which comprises coextrusion of at least two compositions which in each case comprise a thermoplastic, physiologically acceptable polymeric binder which is soluble or swellable in a physiological environment, and at least one of which contains a pharmaceutical active ingredient, and shaping the coextruded multilayer material to the required drug form, and to the drug forms obtainable by this process.

Figure 2:
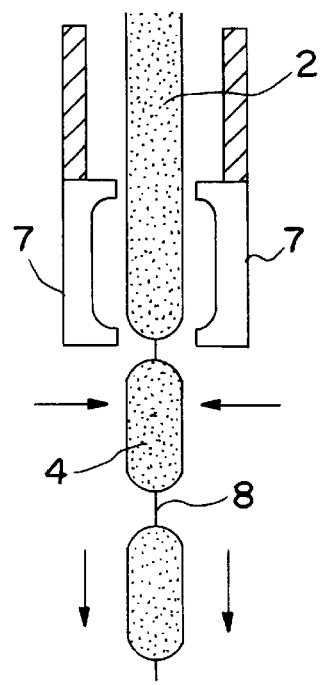

FIG. 1 shows a diagrammatic sectional representation of the coextrusion and shaping of tablets using a molding roll FIG. 2 shows a diagrammatic sectional representation of the shaping of tablets with a pinch device.

Solid drug forms for oral and rectal administration include, in particular, tablets, coated tablets, pastilles and pellets, and suppositories.

The drug forms produced according to the invention are preferably designed so that the outer layer (the outer layers) is (are) not a membrane but is (are) soluble and/or swellable in the body fluid and, where appropriate, represents a protective or adhesive layer.

The drug forms which can be produced according to the invention preferably comprise two or three layers. They can be in open or closed form, in particular as open or closed multilayer tablet.

At least one of the layers contains at least one pharmaceutical active ingredient. It is also possible for another active ingredient to be accommodated in another layer. This has the advantage that two active ingredients which are incompatible with one another can be processed, or that the release characteristics of the active ingredient can be controlled. For example, it is possible to provide an initial dose by including an active ingredient in one of the outer layers, and a maintenance dose by including the active ingredient in the inner layer(s).

The thickness of the layers can be chosen depending on the required release characteristics. The delay of release of the active ingredient increases with the thickness of the layer, ie. the effect lasts longer.

The drug forms according to the invention are particularly suitable for bringing about what is called colon targeting. For this purpose, the release of the active ingredient can be controlled in a time-, pH- or enzyme-dependent manner by the choice of appropriate materials. Time-dependent control can be brought about, for example, by the thickness of a layer and/or rapidly or slowly dissolving materials. Relatively rapid dissolving takes place with, for example, polyvinylpyrrolidone, and relatively slow dissolving takes place with ethylcellulose, polyacrylates or polymethacrylates (Eudragit RL, RS).

pH-dependent control can be brought about by using materials which are soluble in gastric fluid (eg. polyvinylpyrrolidone) and/or which are resistant to gastric fluid and soluble in intestinal fluid (eg. cellulose phthalates, polyacrylates or methacrylates (Eudragit L 30 D or S)).

Enzyme-dependent control can be brought about, for example, by using materials which release the active ingredient only on exposure to enzymes in the intestine, such as galactomannans.

The drug forms are produced starting from at least two separate compositions (mixtures) which in each case comprise at least one thermoplastic, pharmacologically acceptable polymeric binder, where appropriate one or more pharmaceutical active ingredients and one or more conventional auxiliaries and which become, due to melting or softening of at least one component, pasty or viscous (thermoplastic) and therefore extrudable. The glass transition temperature of the composition is below the decomposition temperature of all the components present in the composition. The binder should preferably be soluble or swellable in a physiological environment. Examples of suitable binders are polyvinylpyrrolidone (PVP), copolymers of N-vinylpyrrolidone (NVP) and vinyl esters, especially vinyl acetate, copolymers of vinyl acetate and crotonic acid, partially hydrolyzed polyvinyl acetate, polyvinyl alcohol, poly(hydroxyalkyl acrylates), poly(hydroxyalkyl methacrylates), polyacrylates and polymethacrylates (Eudragit types), copolymers of methyl methacrylate and acrylic acid, cellulose esters, cellulose ethers, especially methylcellulose and ethylcellulose, hydroxyalkylcelluloses, especially hydroxypropylcellulose, hydroxyalkylalkylcelluloses, especially hydroxypropylethylcellulose, cellulose phthalates, especially cellulose acetate phthalate and hydroxypropylmethylcellulose phthalate, starch, starch derivatives, eg. maltodextrins, sugar alcohols, such as mannitol or palatinose, and mannans, especially galactomannans. The K values (according to H. Fikentscher, Cellulose-Chemie 13 (1932), 58–64 and 71–74) of the polymers are in the range from 10 to 100, preferably 12 to 70, in particular 12 to 35, and for PVP preferably 12 to 35, in particular 12 to 17.

Preferred binders for accommodating an active ingredient are polyvinylpyrrolidone, copolymers of N-vinylpyrrolidone and vinyl esters, and hydroxyalkyl acrylates.

Preferred binders for layers containing no active ingredient are binders which are insoluble in aqueous medium or at pH<5, in particular hydroxyalkylcelluloses, alkylcelluloses, hydroxyalkylalkylcelluloses, polyacrylates, cellulose phthalates, polylactides and galactomannans.

The polymeric binder must soften or melt in the complete mixture of all the components in the range from 50 to 180, preferably 60 to 130, ° C., so that the composition can be extruded. The glass transition temperature of the mixture must therefore be below 180° C., preferably below 130° C. If necessary, it is reduced by conventional pharmacologically acceptable plasticizing auxiliaries such as long-chain alcohols, ethylene glycol, propylene glycol, glycerol, trimethylolpropane, triethylene glycol, sugar alcohols, eg. butanediols, pentanols, such as pentaerythritol or hexanols, polyethylene glycols, polypropylene glycols, polyethylene/propylene glycols, silicones, aromatic carboxylic esters (eg. dialkyl phthalates, trimellitic esters, benzoic esters, terephthalic esters) or aliphatic dicarboxylic esters (eg. dialkyl adipates, sebacic esters, azelaic esters, citric and tartaric esters), fatty acid esters such as glycerol mono-, di- or triacetate or sodium diethyl sulfosuccinate. The plasticizer concentration is generally from 0.5 to 15, preferably 0.5 bis 5% of the total weight of the composition for the particular layer. The mixture preferably comprises no plasticizer.

Examples of conventional pharmaceutical ancillary substances, whose total amount can be up to 100% of the weight of polymer, are extenders or bulking agents such as silicates or diatomaceous earth, magnesium oxide, aluminum oxide, titanium oxide, stearic acid or its salts, eg. the magnesium or calcium salt, methylcellulose, sodium carboxymethylcellulose, talc, sucrose, lactose, cereal or corn starch, potato flour, polyvinyl alcohol, especially in a concentration of from 0.02 to 50, preferably 0.20 to 20, % of the total weight of the composition for the particular layer;

lubricants such as aluminum and calcium stearates, talc and silicones, in a concentration of from 0.1 to 5, preferably 0.1 to 3% of the total weight of the composition for the particular layer;

dyes such as azodyes, organic or inorganic pigments or dyes of natural origin with inorganic pigments in a concentration of from 0.001 to 10, preferably 0.5 to 3, % of the total weight of the composition for the particular layer being preferred;

flowability agents such as animal or vegetable fats, especially in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. Waxes, such as carnauba wax, can also be used. These fats and waxes can advantageously be admixed alone or together with mono- and/or diglycerides or phosphatides, especially lecithin. The mono- and diglycerides are preferably derived from the abovementioned fatty acid types. The total amount of fats, waxes, mono- and diglycerides and/or lecithins is 0.1 to 30, preferably 0.1 to 5, % of the total weight of the composition for the particular layer;

stabilizers such as antioxidants, light stabilizers, hydroperoxide destroyers, radical scavengers, stabilizers against microbial attack.

It is furthermore possible to add wetting agents, preservatives, disintegrants, adsorbents and mold release and blowing agents (cf., for example, H. Sucker et al. Pharmazeutische Technologie, Thieme-Verlag, Stuttgart 1978).

Ancillary substances also mean for the purpose of the invention substances for producing a solid solution with a pharmaceutical active ingredient. Examples of these ancillary substances are pentaerythritol and pentaerythritol tetraacetate, polymers such as polyethylene oxides and polypropylene oxides and their block copolymers (Poloxamers), phosphatides such as lecithin, homo- and copolymers of vinyl pyrrolidone, surfactants such as polyoxyethylene 40 stearate, and citric acid and succinic acid, bile acids, sterols and others as indicated, for example, by J. L. Ford, Pharm. Acta Helv. 61, 69–88 (1986).

The only precondition for suitability of ancillary substances is adequate temperature stability.

Pharmaceutical active ingredients means for the purpose of the invention all substances with a pharmaceutical effect and minimal side effects as long as they do not decompose under the processing conditions. The amount of active ingredient per dose unit and the concentration may vary within wide limits depending on the efficacy and release rate. The only condition is that they are sufficient to achieve the required effect. Thus, the active ingredient concentration can be in the range from 0.1 to 95, preferably from 20 to 80, in particular 30 to 70, % by weight. Combinations of active ingredients, eg. ibuprofen/caffeine, can also be employed. Active ingredients for the purpose of the invention are also vitamins and minerals, and crop treatment agents and insecticides. The vitamins include the vitamins of the A group, of the B group, which means, besides $B_1$, $B_2$, $B_6$ and $B_{12}$ and nicotinic acid and nicotinamide, also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutric peptides.

The process according to the invention is suitable, for example, for processing the following active ingredients:

acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefatroxil, cefazolin, cefixime, cefotaxime, ceftazidime, ceftriaxone, cefuroxime, selegiline, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphen, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavine mononucleotide, fluconazole, flunarizine, fluorouracil, fluoxetine, flurbiprofen, furosemide, gallopamil, gemfibrozil, gentamicin, Ginkgo biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenoxymethylpenicillin, phenylephrine, phenylpropanolamine, phenytoin, piroxicam, polymyxin B, povidone iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatotropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, folinic acid, zidovudine.

Preferred active ingredients are ibuprofen (as racemate, enantiomer or enriched enantiomer), ketoprofen, flurbiprofen, acetylsalicylic acid, verapamil, paracetamol, nifedipine or captopril.

There may specifically be the formation of solid solutions. The term "solid solutions" is familiar to the skilled worker, for example from the literature cited at the outset. In solid solutions of pharmaceutical active ingredients in polymers, the active ingredient is present in the form of a molecular dispersion in the polymer.

Before the coextrusion, the composition must be prepared separately for each layer of the drug form. For this purpose, the starting components are processed without solvent in a separate extruder or melt container with downstream gear pump. This may entail the components being fed in singly or as dry mixture continuously (eg. via differential weigh feeders). Then mixing and/or softening or melting of the composition takes place in the extruder or melt container. If it is wished to incorporate in a particular temperature-sensitive active ingredient, this is expediently added only after the softening or melting of the composition and is incorporated by longitudinal and transverse mixing in the extruder or in a kneader or mixing reactor and homogenized with the composition. An extruder, especially a twin screw extruder or single screw extruder with mixing section, is particularly expedient for preparing the composition because this permits operation under conditions which are optimal for the specific material. For example, a different processing temperature can be selected for each layer.

The molten or plastic compositions from the individual extruders or other units are passed into a joint coextrusion die, and extruded. The shape of the coextrusion die depends on the required drug form. For example, dies with a plain die gap, called slot dies, and dies with an annular slit are suitable. The die design moreover depends on the polymeric binder used and the required drug form.

Shaping to the required drug form takes place downstream of the coextrusion die. It is possible to produce a large number of shapes, depending on the coextrusion die and the type of shaping. For example, open multilayer tablets can be produced from an extrudate from a slot die, which has, in particular, two or three layers, by punching or cutting out, eg. using an incandescent wire. Alternatively, open multilayer tablets can be separated via a die with an annular slit by cutting or chopping the extrudate immediately after extrusion or, preferably, by cutting or chopping the extrudate after at least partial cooling.

Closed drug forms, ie. drug forms in which the layer containing active ingredient is completely surrounded by a layer free of active ingredient, are obtained in particular using a die with an annular slit by treating the extrudate in a suitable pinch device as shown, for example, in FIGS. 1 and 2, which is explained in the following examples. It is advantageous in this connection for the inner layer of the multilayer tablet, after the outer layer has cooled, still to be plastically deformable on entry into the pinch device. It is possible in this way to produce, in particular, tablets, preferably oblong tablets, coated tablets, pastilles and pellets.

The multilayer drug forms can be rounded and/or provided with a coating by conventional methods in a downstream step. The rounding is preferably effected by rolls, belts and presses and the coating by treatment in coating pans or fluidized bed apparatus.

It is thus possible with the process according to the invention to produce in a particularly simple and mild manner solid drug forms for oral and rectal administration. In addition, the process provides the possibility of adjusting the required release characteristics in a wide range by the choice of the drug form and the structure thereof and by the choice of the polymeric binder.

The following examples illustrate the invention without restricting it.

EXAMPLE 1

10 kg/h hydroxypropylcellulose (Klucel F) are continuously metered and melted through a twin-screw extruder (ZSK 25 type). In parallel with this, 30 kg/h polyvinylpyrrolidone (PVP) which contains 30% by weight ibuprofen as active ingredient are prepared in another twin-screw extruder (ZSK 30). These extrudates are extruded through a concentric coextrusion die with an annular slit to produce an extrudate consisting of a PVP core containing active ingredient and a Klucel covering, under the following conditions:

| ZSK 30 extruder: | | ZSK 25 extruder: | |
|---|---|---|---|
| Section 1: | 43° C. | Section 1: | 70° C. |
| Section 2: | 57° C. | Section 2: | 120° C. |
| Section 3: | 120° C. | Section 3: | 110° C. |
| Section 4: | 100° C. | Section 4: | 100° C. |
| Section 5: | 100° C. | Section 5: | 100° C. |
| Head: | 100° C. | Head: | 110° C. |
| Die: | 100° C. | Die: | 100° C. |

This extrudate is then separated into closed oblong tablets by the pinch device shown in FIGS. 1 and 2. In FIG. 1, the coextrusion die is identified by 1. The extrudate 2 emerging from the die (the individual layers are not shown in the figure) is passed into a calender with two counter-rotating molding rolls 3. The molding rolls have depressions 5 which are separated by bars 6. The distance between the molding rolls 3 is chosen so that they contact one another along a line on one of the bars 6 or so that there is only a very small distance. The shape of the depressions 5 can be chosen within a wide range so that numerous drug forms can be produced in this way.

The extrudate 2 emerging from the coextrusion die 1 is received in the depressions 5 and separated into individual drug forms by the bars 6. Using the device shown in FIG. 1, oblong tablets 4 which are still connected by the flash 8 are obtained in this way.

Alternatively, the pinching can take place with the device shown in FIG. 2. The product extrudate 2 emerging from the coextrusion die is passed into a device which has two pinch bars 7 which are mutually opposite and enclose the extrudate 2. The pinch bars 7 can be moved perpendicular to the extrudate 2 (indicated by the arrows in FIG. 2) and have mutually opposite depressions corresponding to the depressions on the calender rolls 3 in FIG. 1. In order to separate the drug form, the pinch bars 7 are moved towards the extrudate 2 until they are in contact with one another or only a very small distance remains. This results in separation of the drug form, although the individual drug forms are still connected by a flash 8. Closed oblong tablets are likewise obtained using the device shown in FIG. 2.

The resulting oblong tablets can be deflashed in a conventional way, for example in rotating pans.

The Klucel outer covering of the resulting oblong tablets results in slower release of the active ingredient dispersed in the PVP core.

EXAMPLE 2

Tablets which contain ibuprofen in the core and caffeine in the outer layer are obtained by the process indicated in Example 1 and using the materials described therein, with the hydroxypropylcellulose containing 5% caffeine.

EXAMPLE 3

10 kg/h of a mixture of hydroxypropylcellulose and ethylcellulose in the ratio 8:1 by weight is continuously metered and melted in a twin-screw extruder (ZSK 25 type). In parallel with this, 15 kg/h polyvinylpyrrolidone which contains 40% by weight paracetamol as active ingredient are prepared in a second twin-screw extruder (ZSK 30). 15 kg/h hydroxypropylcellulose melt which contains 40% by weight paracetamol as active ingredient are conveyed by a gear pump in a third extrudate.

These extrudates are extruded through a concentric annular coextrusion die to produce an extrudate consisting of a hydroxypropylcellulose core with a low release rate, a surrounding layer of polyvinylpyrrolidone with a high release rate and a hydroxypropylcellulose/ethylcellulose covering (the extrusion conditions are as indicated in Example 1).

The extrudate is separated into individual closed tablets by the pinch device shown in FIG. 1 or FIG. 2.

The kinetics of release of the active ingredient can be controlled optimally by the resulting multilayer tablet to increase patient compliance.

EXAMPLE 4

15 kg/h polyvinylpyrrolidone, which contains 30% by weight nifedipine as active ingredient are prepared in a twin-screw extruder (ZSK 30 type). In parallel with this, 15 kg/h hydroxypropylcellulose melt which contains 40% by weight nifedipine as active ingredient are conveyed by a gear pump in another extrudate.

The two extrudates are extruded through a slot die (3 slots) to result in a composition with sandwich structure which consists of a hydroxypropylcellulose layer which has a low release rate and is surrounded on both sides by a polyvinylpyrrolidone layer with a high release rate (extrusion conditions as indicated in Example 1).

The extrudate is separated into open multilayer tablets by a punching device.

In a subsequent step, the resulting open multilayer tablets can be coated with an acrylic acid copolymer in a coating pan.

The kinetics of release of the active ingredient can be controlled optimally by the sandwich structure of the multilayer tablet to increase patient compliance.

EXAMPLE 5

An extrudate is produced by the process indicated in Example 1 and using the material indicated therein and is separated into open multilayer tablets by a suitable cold cut device. The Klucel outer covering results in a slower release of the active ingredient dispersed in the PVP core.

EXAMPLE 6

An extrudate consisting of a hydroxypropylcellulose core with a low release rate, a surrounding layer of polyvinylpyrrolidone with a high release rate and an outer layer of hydroxypropylcellulose/ethylcellulose is produced using the materials described in Example 3 and by the process described therein. This extrudate is separated by a cold cut device into individual open multilayer tablets.

The kinetics of release can be controlled optimally by this arrangement of the multilayer tablet to increase patient compliance.

EXAMPLE 7

10 kg/h polylactide are continuously metered and melted through a twin-screw extruder (ZSK 25 type). In parallel with this, 30 kg/h polyvinylpyrrolidone which contains 40% by weight ibuprofen as active ingredient are prepared in another twin-screw extruder (ZSK 30 type). The two extrudates are extruded through an annular coextrusion die to result in an extrudate which consists of a PVP core containing active ingredient and a polylactide covering (extrusion conditions as indicated in Example 1).

This extrudate is separated in a cold cut device into individual open multilayer tablets.

The polylactide covering is stable to hydrolysis and can be decomposed both enzymatically and by hydrolysis so that the active ingredient can be released from the core matrix.

EXAMPLE 8

10 kg/h vinylpyrrolidone/vinylacetate (6:4) copolymer (30% by weight) with 40% by weight mannitol and 30% by weight verapamil are melted in a twin-screw extruder (ZSK 25). In parallel with this, 30 kg/h hydroxypropylcellulose which contains 30% by weight verapamil as active ingredient are prepared in another twin-screw extruder (ZSK 30).

The two extrudates are extruded through an annular coextrusion die under the conditions specified in Example 1. The shaping to tablets takes place by the method indicated in Example 1 using the device shown in FIG. 2. The tablets consist of a hydroxypropylcellulose core containing active ingredient and a vinylpyrrolidone/vinyl acetate copolymer/mannitol covering.

EXAMPLE 9

Tablets which have a hydroxypropylcellulose core (hydroxypropylcellulose with a low degree of substitution, LH 31 type) with vitamin A and E and a hydroxypropylcellulose covering (Klucel F) with vitamin C are produced by the process indicated in Example 2.

We claim:

1. A process for producing multilayer, solid drug forms for oral or rectal administration, which comprises coextrusion of at least two compositions which in each case comprise a thermoplastic, pharmacologically acceptable polymeric binder which is soluble or swellable in a physiological environment, and at least one of which contains a pharmaceutical active ingredient, and shaping the coextruded multilayer material to the required drug form.

2. A process as claimed in claim 1, wherein the polymeric binder for a layer containing no active ingredient is selected from the group consisting of hydroxyalkylcelluloses, alkylcelluloses, hydroxyalkylalkylcelluloses, cellulose phthalates, polyacrylates, galactomannans and polylactides.

3. A process as claimed in claim 1, wherein the polymeric binder for a layer containing active ingredient is selected from the group consisting of polyvinylpyrrolidones, copolymers of N-vinylpyrrolidone and vinyl esters and hydroxyalkyl acrylates.

4. A process as claimed in claim 1, wherein an active ingredient which is selected from the group consisting of ibuprofen, ketoprofen, flurbiprofen, acetylsalicylic acid, verapamil, paracetamol, nifedipine, caffeine, captopril and vitamins or mixtures of two or more of these active ingredients is used.

5. A process as claimed claim 1, wherein to produce closed drug forms the coextrusion is carried out with a concentric annular coextrusion die and the shaping is carried out in a molding calender or by a hot or cold cut method.

6. A process as claimed in claim 1, wherein to produce open drug forms, especially open multilayer tablets, the coextrusion is carried out using a slot die and the shaping is carried out by punching.

7. A process as claimed in claim 5, wherein hydroxypropylcellulose is used as polymeric binder for the outer layer(s), and polyvinylpyrrolidone is used for the inner layer and the core.

8. A process as claimed in claim 5, wherein ibuprofen alone or ibuprofen/caffeine or vitamins A, C, E are used as active ingredient, with the ibuprofen or the vitamins A and E being located in the core and the caffeine or the vitamin C being located in the outer layer.

9. A process as claimed in claim 1, wherein the multilayer drug forms are, in a subsequent step, rounded and/or provided with a coating.

10. A multilayer solid drug form for oral or rectal administration obtainable by a process as claimed in claim 1.

* * * * *